United States Patent
Brown et al.

(10) Patent No.: US 7,430,773 B2
(45) Date of Patent: Oct. 7, 2008

(54) DEVICE TO FACILITATE CONTROLLED ROTATION OF THE CERVICAL SPINE

(75) Inventors: Micah B. Brown, Westerville, OH (US); Jon A. Cappel, Monroe, WI (US); Kevin M. Johnson, Madison, WI (US); Matthew R. Smith, Greenfield, WI (US); Noelle C. Simatic, Greenfield, WI (US); Arinne N. Lyman, Waterford, WI (US); Victor M. Haughton, Oconomowoc, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 374 days.

(21) Appl. No.: 11/231,011

(22) Filed: Sep. 20, 2005

(65) Prior Publication Data

US 2007/0061972 A1     Mar. 22, 2007

(51) Int. Cl.
    *A61G 13/12* (2006.01)
(52) U.S. Cl. .................... 5/601; 5/622; 5/637
(58) Field of Classification Search .......... 5/601, 5/622, 636, 637, 640; 378/20, 208, 209; 600/407, 410–423, 425–429, 414, 426
    See application file for complete search history.

(56) References Cited

U.S. PATENT DOCUMENTS

| | | | | |
|---|---|---|---|---|
| 3,025,397 A | * | 3/1962 | Travis et al. | 378/208 |
| 3,188,079 A | * | 6/1965 | Boetcker et al. | 5/622 |
| 3,536,913 A | * | 10/1970 | Huchel | 378/40 |
| 4,928,283 A | * | 5/1990 | Gordon | 378/20 |
| 5,078,140 A | * | 1/1992 | Kwoh | 600/417 |
| 5,109,397 A | * | 4/1992 | Gordon et al. | 378/205 |
| 5,448,608 A | * | 9/1995 | Swain et al. | 378/4 |
| 5,675,851 A | * | 10/1997 | Feathers | 5/632 |
| 5,735,278 A | * | 4/1998 | Hoult et al. | 600/422 |
| 6,813,788 B2 | * | 11/2004 | Dinkler et al. | 5/622 |
| 6,863,440 B2 | * | 3/2005 | Sildve et al. | 378/208 |
| 2006/0115055 A1 | * | 6/2006 | Marino | 378/208 |

OTHER PUBLICATIONS

Appel, B.L., et al., Isocentric Neck Rotator for MRI and CT; admitted prior art, Dec. 10, 2003, Madison, Wisconsin.

* cited by examiner

*Primary Examiner*—Patricia Engle
*Assistant Examiner*—Gilbert Y Lee
(74) *Attorney, Agent, or Firm*—Boyle Fredrickson, S.C.

(57) ABSTRACT

A device for controlled orientation of a person's cervical spine that is compatible with medical imaging machines. The device is capable of rotation about the axis of a patient's spinal column independent of, or in addition to, flexion/extension of a patient's spinal column. The device may incorporate locking mechanisms to secure rotational orientation and may include quantitative indicators of the degree of rotation.

19 Claims, 5 Drawing Sheets

DEVICE TO FACILITATE CONTROLLED ROTATION OF THE CERVICAL SPINE

BACKGROUND OF THE INVENTION

The present invention relates generally to a medical-imaging compliant apparatus for adjusting a patient's head position to facilitate controlled orientation of the cervical spine during medical imaging.

Medical imaging has become an indispensable tool for the diagnosis and treatment of conditions affecting a person's cervical spine. Images of the cervical spine provide doctors with insight into such conditions as cerebral spinal fluid flow patterns, nerve compression, spinal instability and intervertebral disk damage. Diagnosis of these, and other conditions, often requires that images of the patient's spine be taken while the spine is rotated about its axis or while undergoing flexion/extension. These specific configurations may need to be accurately recreated during subsequent imaging to facilitate diagnosis and treatment.

Medical imaging technologies, such as those used in magnetic resonance ("MR") imaging and computed tomography ("CT") imaging, are extremely sensitive to the amount and type of material, as well as its location in relation to the area to be imaged, of any equipment present during imaging. MR imaging uses a strong magnetic field to polarize nuclei whose position is then detected by special coils. The presence of conductive or magnetic material disrupts the detection and thus spatial encoding of the signals—ultimately degrading the clarity of the image and the information the doctor is able to learn from the MR scan.

CT imaging uses X-ray attenuation to reconstruct a three-dimensional image. Given that different materials and tissues cause varying attenuation of the X-rays used in a CT, it is critical that any support structure introduced into the scan be radiolucent, meaning the material does not substantially scatter or block the X-rays causing artifacts in the images.

Conventional wisdom has lead inventors to design cervical rotation devices that remove supporting structure from the area to be imaged to reduce image artifacts. When the material is unable to be removed from the imaging area, plastics are commonly used because of their low interaction with both MR and CT imaging machines. The removal of structure from the imaging area along with the use of imaging compliant materials is advantageous as it reduces the amount of interference caused by the fixture, therefore providing a more informative image.

One previous design consists of a head cradle shaped as a half-cylinder with one open end and one closed end. A pin mounted to the closed end supports the head cradle. The other end of the pin is rotatably mounted to the back of a frame having support legs extending on the left, back, and right of the head cradle minimizing the portion of the support structure within the imaging area of the head cradle. The design is effective at removing the majority of the structure from the imaging area; however, a single pin supports the entire weight of the patient's head. This cantilevered design places a tremendous amount of stress on the pin making it less suited for construction from CT and MR imaging compliant materials such as plastic. Additionally, orientating a patient's head is difficult given the high load placed upon the pin at the axis of rotation.

Another design incorporates an outer ring with radial slots around a portion of the circumference. A head cradle shaped as an open-ended half-cylinder has two collinear pegs extending radially outward from the head cradle. The head cradle is suspended within the large outer ring by placing the two pegs through the radial slots in the outer ring and independently clamping each peg in place. This design eliminates the high stresses placed on the single pin in the previous design, but the head cradle may be difficult to rotate because the weight of the patient's head acts to wedge the pegs downward in the radial slots.

It is critical that the portion of the spine being imaged remains immobile in the desired orientation throughout imaging. Common techniques to reduce head movement during imaging involve combinations of strategically located straps, clamps, and blocks. These techniques are time consuming and cumbersome because a health care professional must configure the individual pads and straps. The sight of clamps and straps may add to patient anxiety.

BRIEF SUMMARY OF THE INVENTION

The present inventors have determined that placing a bearing surface substantially beneath the patient's head allows a sturdy and relatively rigid support to be constructed of lightweight, non-metallic materials that do not substantially interfere with the CT or MRI imaging process. Furthermore, the present inventors have recognized that a head support pad having a sufficient configuration and compliance can comfortably and unobtrusively maintain a patient's head position during rotation of the fixture during imaging.

Specifically, the invention provides a fixture for adjusting a patient's head position in a medical imaging machine having a base supporting a head cradle defining a volume receiving and supporting a patient's head. The fixture also has a bearing, having first and second bearing surfaces moving with respect to each other about a first axis aligned with the patient's neck, the bearing is located between the base and the head cradle along a vertical line passing substantially through a center of mass of the patient's head when the head is at a predetermined position in the head cradle. The bearing is constructed of a material that is substantially transparent to the imaging machine.

It is thus one object of at least one embodiment of the invention to provide a support for rotation of a patient's cervical spine that is both sturdy and compliant with medical imaging technologies. The bearing surface beneath the head allows use of radiolucent and nonferrous material to provide sturdy support and smooth rotation.

The base may include a cradle support mounted to rotate about a second axis perpendicular to the first axis.

Thus, it is another object of at least one embodiment of the invention to adjust the flexion and extension of a patient's cervical spine before axial rotation.

The fixture may further include a first handle communicating with the head cradle to selectively rotate the head cradle about the first axis.

It is thus another object of at least one embodiment of the invention to provide a convenient means of rotating the patient's head.

The first handle may also selectively rotate the cradle support about the second axis.

Thus, it is another object of at least one embodiment of the invention to provide a single means of controlling the rotation and flexion/extension of a patient's cervical spine.

The first handle may include a first lock actuated by the first handle that selectively prevents rotation of the head cradle about the first axis.

It is thus another object of at least one embodiment of the invention to provide a single control that facilitates rotation about the axis of a patient's cervical spine and locks the fixture in the desired position.

The first lock may be a threaded member that is rotated to clamp the cradle support and the head cradle.

Thus, it is another object of at least one embodiment of the invention to provide a simple and reliable lock mechanism that provides both mechanical advantage and allows for secure positioning about the axis of a patient's cervical spine over a range of orientations.

The fixture may further include a second lock that selectively prevents rotation of the cradle support about the second axis.

It is thus another object of at least one embodiment of the invention to separate the rotational locks to allow rotation about one axis independent of rotation about the other axis.

The second lock may be a threaded member that is rotated to clamp the base to the cradle support.

Thus, it is another object of at least one embodiment of the invention to provide a lock mechanism that provides a mechanical advantage and allows for secure flexion/extension positioning of a patient's cervical spine in an infinite number of orientations.

The fixture may have a base configured to engage a medical imaging table.

It is thus another object of at least one embodiment of the invention to provide a fixture that may be installed on a variety of machines.

The fixture may include a first scale indicating rotation about the first axis from a predetermined position.

Thus, it is another object of at least one embodiment of the invention to provide for quantitative measurement of the amount of rotation of the device about the axis of a patient's cervical spine.

The fixture may include a second scale indicating rotation about the second axis from a predetermined position.

It is thus another object of at least one embodiment of the invention to provide for quantitative measurement of the amount of flexion/extension of a patient's cervical spine.

The fixture may further include a first marker mounted to the cradle support wherein the first marker is configured to be detected by a medical imaging device.

Thus, it is another object of at least one embodiment of the invention to provide an indication of the position of the cradle support that will be preserved in the final image to aid in diagnostics.

The fixture may further include a second marker mounted to the head cradle wherein the second marker is configured to be detected by a medical imaging device.

It is thus another object of at least one embodiment of the invention to provide an indication of the position of the head cradle that will be preserved in the final image to aid in diagnostics.

The bearing may also present a portion of a surface of a cylinder, the cylinder being coaxial about the first axis.

Thus, it is another object of at least one embodiment of the invention to have a bearing surface that provides isocentric rotation and approximates the general shape of the back of a patient's head to decrease the height of the head cradle while providing a broad area of contact.

The fixture may further include a mat sized and arranged to align the first axis and the axis of a patient's spine.

It is another object of at least one embodiment of the invention to provide a simple method for aligning the axis of a patient's spine to allow for pure rotation of the patient's cervical spine while allowing the bearing to be placed below the head surface.

The mat may be independent of the base.

Thus, it is another object of at least one embodiment of the invention to have a mat that can be manipulated independently of the fixture to allow for interchangeability of the mat to accommodate different patients.

Additionally, the invention provides a fixture for adjusting a patient's head position in a medical imaging machine having a base, a cradle support mounted to the base, and a head cradle communicating with the cradle support. The fixture also has a head support pad attached to the head cradle or the cradle support. The head support pad has a concave cross-section with a compliance that applies sufficient lateral pressure upon the temporal region of a patient's head, under the weight of an average patient's head, to substantially maintain the patient's head placement relative to the head cradle throughout movement of the head cradle and cradle support.

It is thus another object of at least one embodiment of the invention to provide a convenient device to stabilize a patient's head position during medical imaging.

Furthermore, the invention provides a fixture for adjusting a patient's head position in a medical imaging machine comprising a base, a first support and a second support attached to the base and extending upwardly from the base, an outer ring rotatably mounted between the first and the second supports having a first central axis and an inner surface sized to encompass a patient's head. Furthermore, the fixture has an inner ring having a second central axis and an outer surface sized to fit rotationally within the outer ring, wherein the first and second central axes are aligned.

Thus, it is another object of at least one embodiment of the invention to provide a device easily manufactured from rotatably engaged concentric rings rotatably mounted between side supports.

The fixture described above may further include a rollable bearing element and a first race sized to engage the bearing formed in the inner surface of the outer ring, the outer surface of the inner ring, or both.

It is thus another object of at least one embodiment of the invention to have a device with smooth and continuous rotation to promote patient comfort and ease of use.

The rollable bearing element may be a ball.

Thus, it is another object of at least one embodiment of the invention to be readily manufactured from commonly available plastic ball elements.

These particular objects and advantages may apply to only some embodiments falling within the claims and thus do not define the scope of the invention.

DETAILED DESCRIPTION OF THE PREFERRED EMBODIMENT

Figure 1:
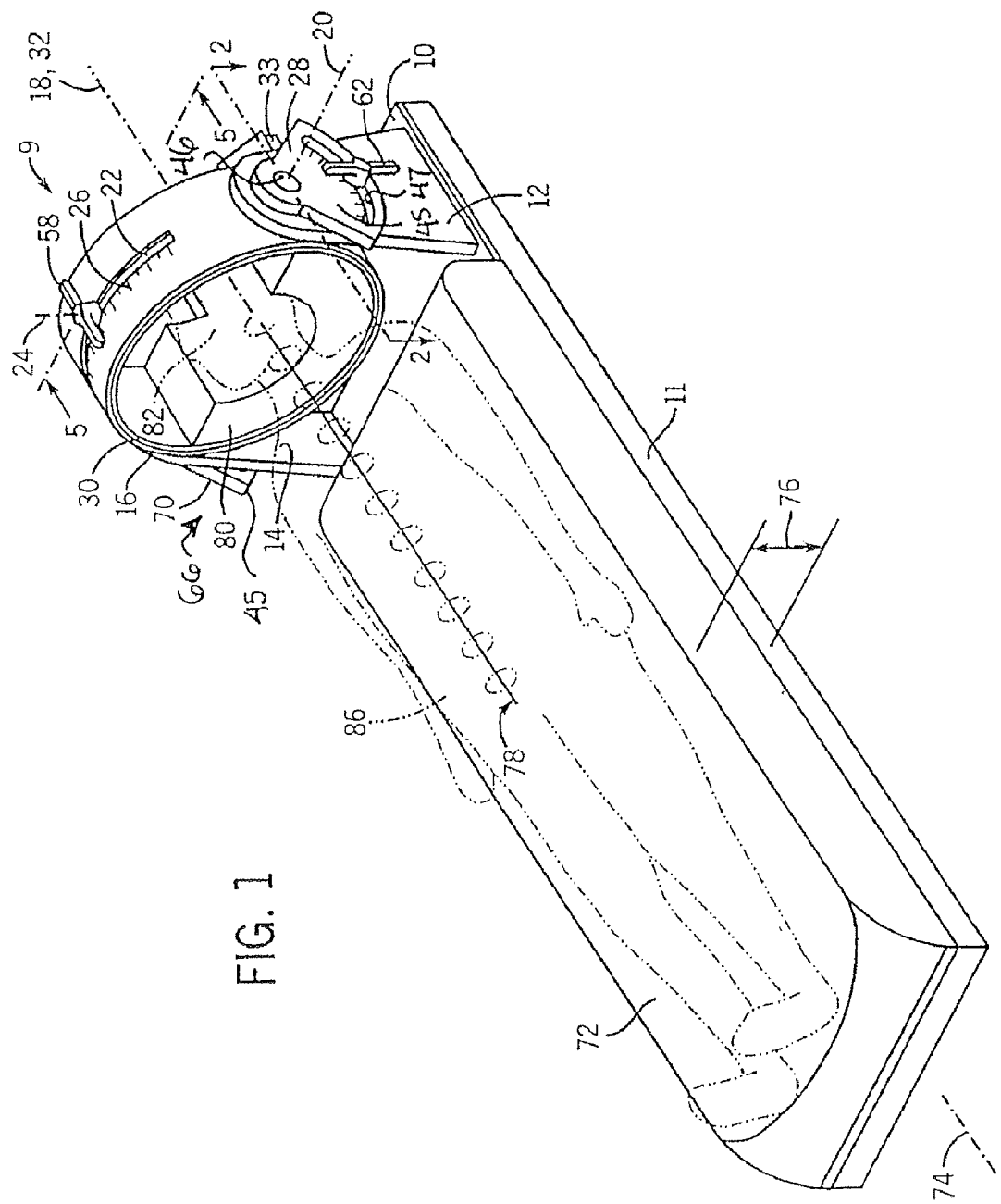
FIG. 1 is a perspective view of the present invention providing a fixture for rotating a patient's head axially in a medical imaging machine.

With reference to FIG. 1, the cervical spine rotation fixture 9 constructed according to the present invention has a generally rectangular base 10 with a planar upper surface and a convex lower surface configured to engage a variety of medical imaging machine tables 11, including a magnetic resonance ("MR") imaging machine or a computed tomography ("CT") imaging machine.

A left pillar 12 and a right pillar 14 are attached in opposition at left and right sides of the base 10 and extend upwardly from the base 10 parallel to each other and perpendicular to the base 10. As used herein, directions, such as "left" and "right", will be with respect to a patient 86 lying supine on the patient table 11 with the patient's head above the base 10.

An outer ring 16, having a central axis 18, fits between the left and right pillars 12 and 14 to be supported thereby on a shafts 46 (shown also in FIG. 5) passing through the left and right pillars 12 and 14 so that the outer ring 16 may rotate about a generally horizontal, flexion/extension axis 20 extending between the left and right pillars 12 and 14. Ends of the shafts 46 are attached to plates 45 passing downward along the outer surfaces of the left and right pillars 12 and 14 to rotate with the shafts 46.

An inner ring 30 fits within the outer ring 16 to rotate therein such that the central axis 32 of the inner ring 30 is coaxial with the first central axis 18 of the outer ring 16. The inner ring 30 thus rotates, with respect to the outer ring 16, about the first and second central axes 18 and 32.

The outer ring 16 has a height measured along the central axis 18 of approximately one-half the height of an average human head measured in the superior/inferior direction and diameter slightly greater than the diameter of the average person's head. As shown also in FIG. 3, the inner ring 30 includes a lower shelf portion 33 extending in a superior direction approximately the height of the outer ring 16 beyond the outer ring 16. The remainder of the inner ring is of the same height as the outer ring 16.

The outer ring 16 has a first slot 22 extending approximately 45 degrees circumferentially clockwise and counterclockwise from a vertical axis 24. A handle 58, to be described below, attaches to the inner ring 30 and extends through the slot 22. As shown also in FIG. 4, first scale 26 is affixed to the outer ring 16 to show the degree of axial rotation (angle beta) of the inner ring 30 about the first central axis 18 as indicated by position of the handle 58.

The plates 45 likewise have arcuate slots 47 at a constant radius about axis 20 and of angular extent of approximately 30 degrees. Second handles 62 and 66, also to be described below, attach to the left and right outer surfaces of the left and right pillars 12 and 14, and extend through the slots 47. As shown also in FIG. 3, second scales 28 are affixed to the plates 45 showing the degree of rotation (angle alpha) of the outer ring 16 and inner ring 30 in flexion/extension about axis 20 as revealed by the position of the handles 62 and 66 with respect to the scales 28.

Figure 2:
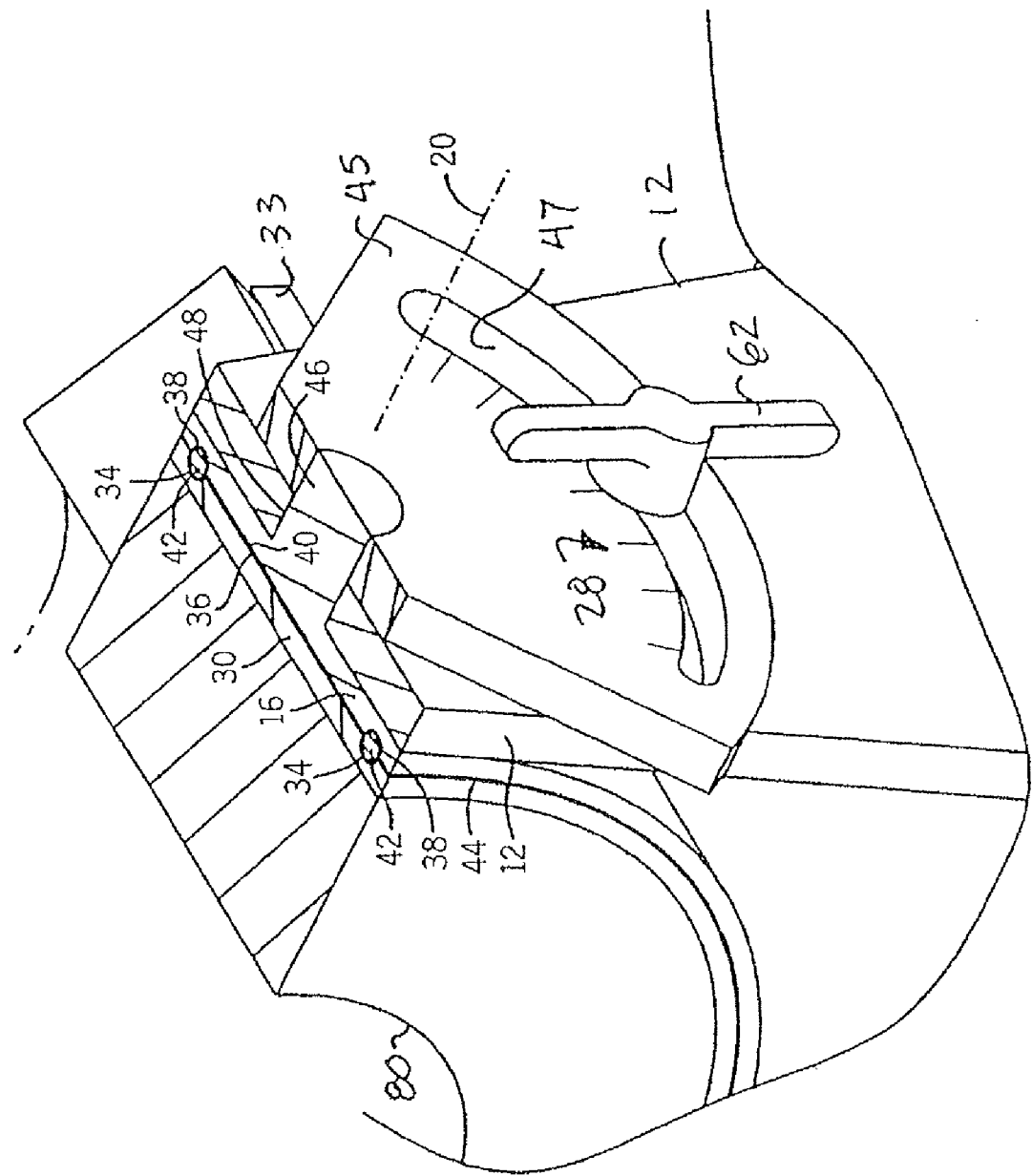
FIG. 2 is a fragmentary section view along line 2-2 of FIG. 1 showing a bearing for flexion/extension adjustment.

Referring now to FIG. 2, the interface between the outer ring 16 and inner ring 30 provides a first and second race formed of opposed hemicylindrical grooves 34, 36 in each of the outer ring 16 and inner ring 30, the grooves following a path coaxial with axes 18 and 32. Each race has a hemicircular cross section approximately equal to the radius of a number of ball bearings 42 that may be placed in opposed grooves 34, 36 to provide a slight gap 44 between the inner ring 30 and the outer ring 16.

Figure 3:
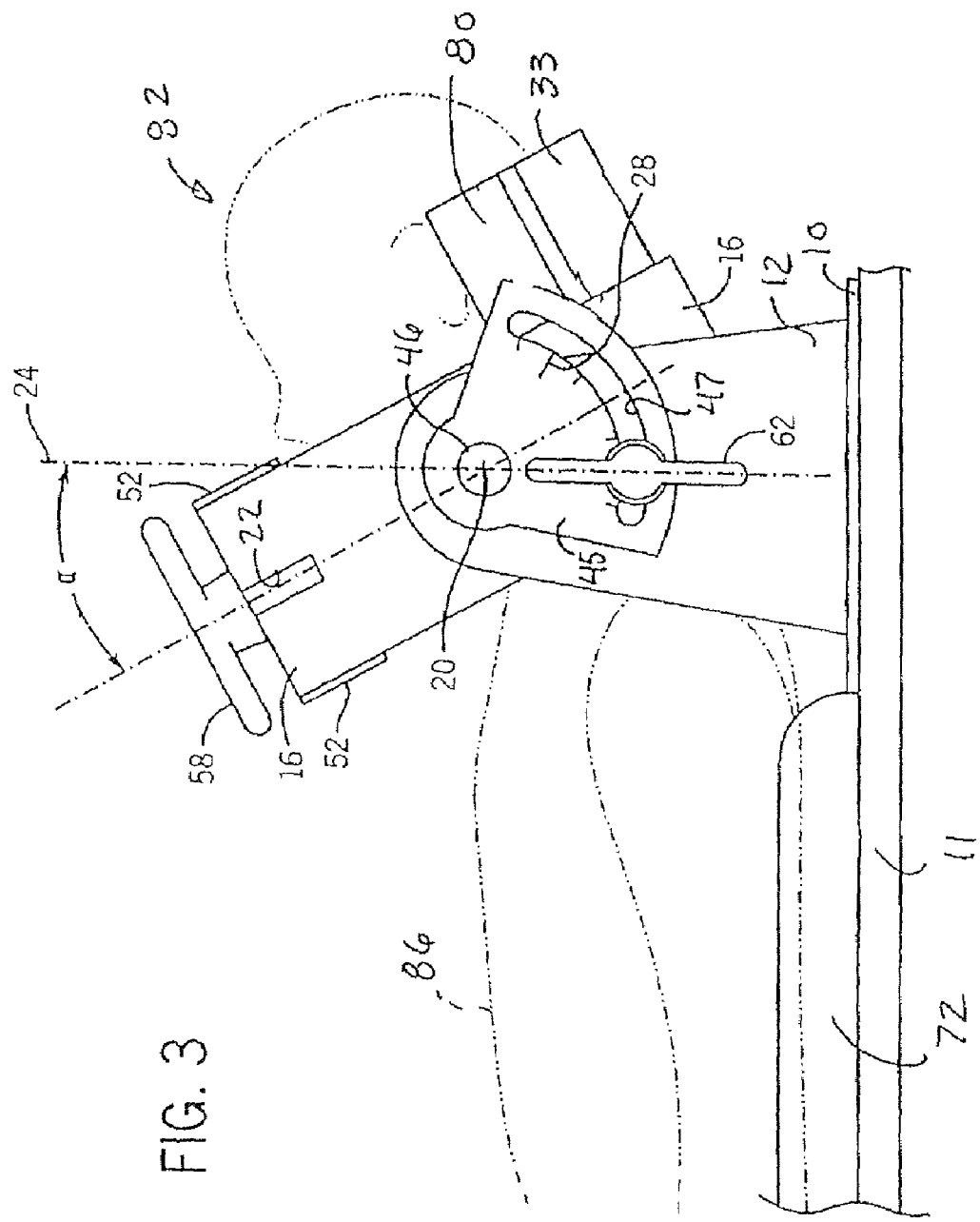
FIG. 3 is a side view showing the fixture rotated to provide flexion of a patient's spine.
Figure 4:
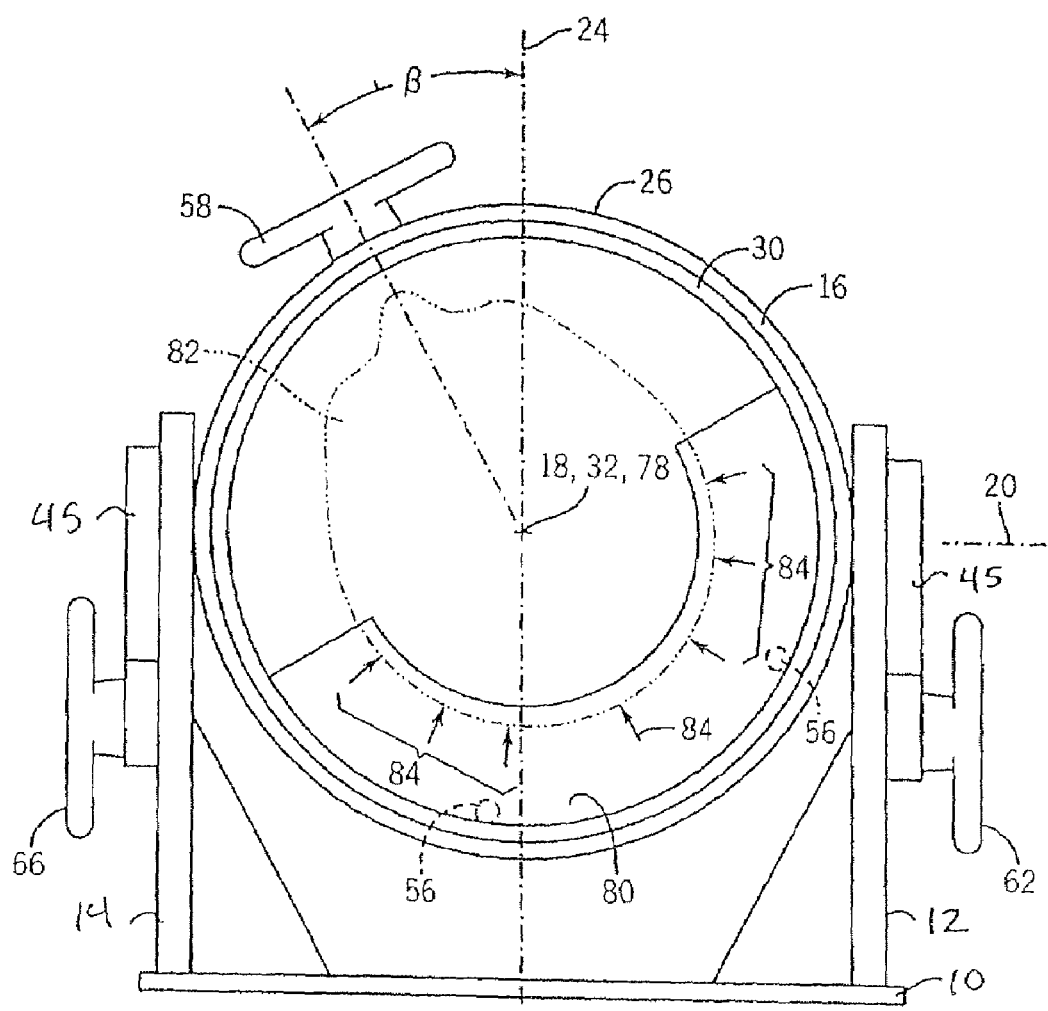
FIG. 4 is a simplified end view of the embodiment of FIG. 1 showing the fixture rotated axially.

As shown in FIG. 3, the outer ring 16 may have fiducial markers 52 mounted in several locations around the circumference of the outer ring 16 to allow the location and flexion/extension orientation of the outer ring 16 to be captured by an imaging machine. The first markers 52 may have a circular cross-section and be constructed of radio opaque material for an x-ray CT or of an NMR contrast material, for example, a mixture of gadolinium and water, for MRI. Referring to FIG. 4, second fiducial markers 56 are mounted parallel to the second central axis 32 on the inner ring 30 to allow the axial orientation of the inner ring 30 to be captured by an imaging machine. The second markers 56 may also have a circular cross-section and be constructed of similar material to the first fiducial markers. The first markers 52 and second markers 56 are generally elongated such that the plane of a cross-sectional image will intersect a portion of the markers 52, 56.

Figure 5:
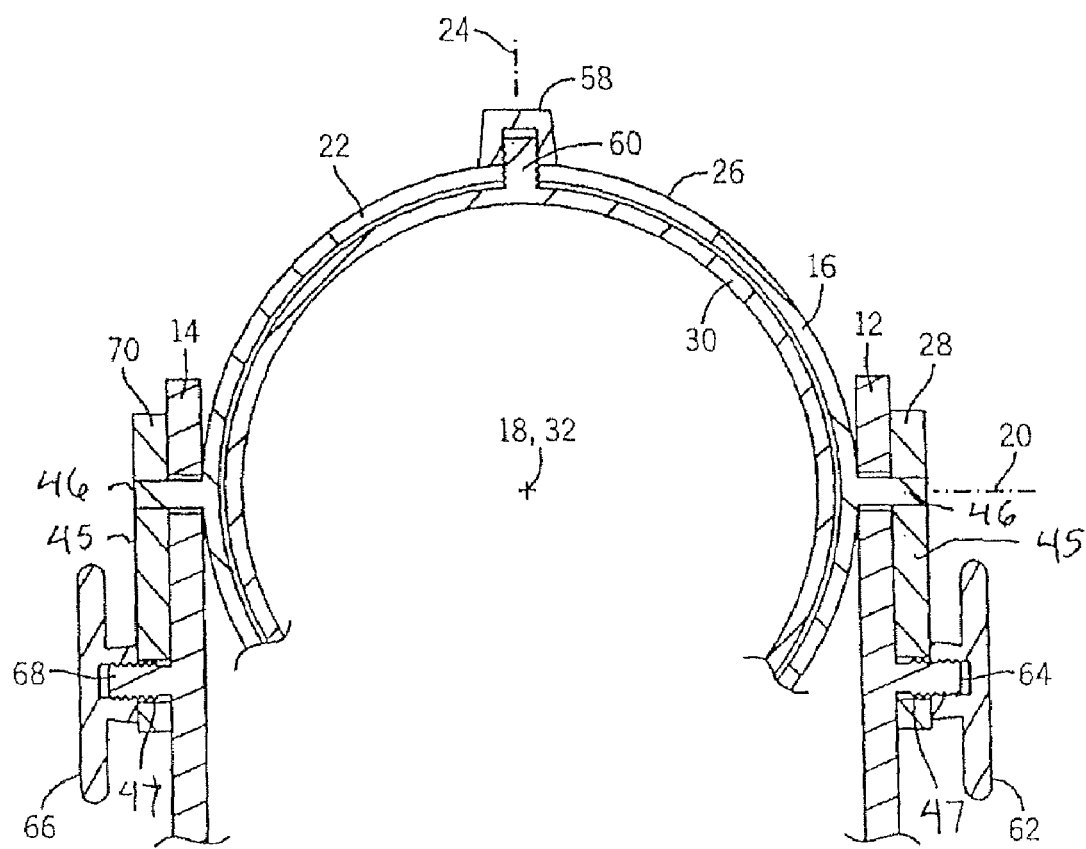
FIG. 5 is a fragmentary section view along line 5-5 of the embodiment of FIG. 1.

Referring now to FIG. 5, relative rotation of the inner ring 30 about the central axes 18, 32 with respect to the outer ring 16 may be locked by rotating handle 58. Handle 58 includes internal threads engaging a threaded stud 60 that extends radially outward from the inner ring 30 through the first slot 22 in the circumference of the outer ring 16. Upon rotating the first handle 58, the inner ring 30 and the outer ring 16 are clamped together.

Likewise, rotation of the outer ring 16 and inner ring 30 about the flexion/extension axis 20 with respect to the left and right pillars 12 and 14 may be locked by turning the second handles 62 and 66. Each of second handles 62 and 66 have internal threads receiving threaded studs 64 and 68, respectively, extending horizontally outward from the left pillar 12 and right pillar 14 through an arcuate slots 47 in the respective plates 45. Rotating these handles 62 and 64, clamps the plates 45 to the respective pillar 12 or 14.

For use in MR imaging, all elements of the fixture can be made from non-ferromagnetic and non-conductive materials such as polycarbonate, acrylic, polypropylene, nylon, and polyvinyl chloride, for example. Additionally, when compliance with CT imaging is desired, the use of radiolucent materials with low mass attenuation coefficients is preferred (e.g., carbon composites).

Returning briefly to FIG. 1, a rectangular mat 72, sized and contoured to comfortably accommodate the body of an average person, has a central longitudinal axis 74 that is oriented parallel to the central axes 18, 32. The mat 72 can be configured to be attached to the base 10 or separate from the base 10. The mat 72 has an appropriate thickness 76 necessary to align the axis of a patient's spinal column 78 with the second central axis 32 of the inner ring 30. In one embodiment, the mat 72 has a thickness 76 of approximately 4 inches. The mat 72 can be made from a variety of materials that provide sufficient comfort and support including, for example, foam, rubber, and plastic. Different mats 72 of different thicknesses can be used for different purposes and patients.

As shown in FIG. 1, the head support pad 80 is sized to substantially encompass the posterior portion of a human head and is attached to the inner ring 30 approximately along the bottom half of the inner ring 30 and the shelf portion 33 of the inner ring 30 that extends beyond the outer ring 16.

Turning to FIG. 4, the head support pad 80 has a substantially concave cross-section and is constructed from a material with a compliance that deforms under the weight of an average patient's head 82. The head support pad 80 supplies a counteracting force 84 around the temporal and posterior regions of the patient's head 82 that stabilizes the patient's head 82 and helps maintain the orientation of the patient's head 82 with respect to the inner ring 30 under rotation about the central axes 18, 32 and with respect to the outer ring 16 under rotation about the flexion/extension axis 20. The head support pad 80 can be made from a material such as polyurethane foam or any other material having a sufficient compliance.

Returning to FIG. 1, during use of the device, the patient is positioned in a supine position on the mat 72 with the patient's spinal column 78 coaxial with the central axis 18, 32 of the inner ring 30 and outer ring 16. The patient's head 82 is placed within the inner ring 30 and secured by the head support pad 80.

Once the patient 86 is secured, a health care professional can easily adjust the patient's head 82 about the flexion/extension axis 20 with one hand on handle 58. Referring again to FIG. 5, to lock the position about the flexion/extension axis 20, the health care professional may use a second hand to tighten one of the second handle 62 and third handle 66. The second scale 28 or third scale 70 provide the health care professional with an indication of the amount of rotation about the flexion/extension axis 20.

Once in the desired position, the health care professional may tighten the second handle 62 and/or third handle 66 to secure the outer ring 16 in place.

To rotate about the patient's spinal column 78, the health care professional may continue to move the first handle 58 while observing the first scale 26. Once the desired axial rotation is reached, the health care professional may tighten the first handle 58 to secure the inner ring 30 in place. FIG. 4 shows the device after rotation about the patient's spinal column 78.

It is specifically intended that the present invention not be limited to the embodiments and illustrations contained herein, but that modified forms of those embodiments including portions of the embodiments and combinations of elements of different embodiments also be included as coming within the scope of the following claims.

We claim:

1. A fixture for adjusting a patient's head position in a medical imaging machine comprising:
   a base having a cradle support;
   a head cradle defining a volume and including a head support for rotating the patient's head with respect to the cradle support; and
   a bearing connecting the cradle support and head cradle, the bearing having a first and second bearing surface moving with respect to each other to rotate the head support and the patient's head about a rotation axis substantially aligned with the patient's neck, the bearing surfaces disposed along a line passing substantially vertically through a center of mass of a patient's head when the head is at a predetermined position in the head cradle;
   wherein the bearing and head cradle are constructed of material that is substantially transparent to the medical imaging machine;
   and wherein the base and head cradle are positionable between an imaging device of the medical imaging machine and the patient's head.

2. The apparatus of claim 1 wherein the base includes a second bearing allowing the head cradle to rotate about a second axis perpendicular to the rotation axis.

3. The apparatus of claim 2 further including a second lock that locks to prevent rotation of the head cradle about the second axis.

4. The apparatus of claim 3 wherein the second lock is a threaded member that is rotated to clamp the base to the head cradle.

5. The apparatus of claim 1 further including a first handle communicating with the head cradle to selectively rotate the head cradle about the first axis.

6. The apparatus of claim 5 further including a first lock actuated by the first handle that selectively prevents rotation of the head cradle about the first axis.

7. The apparatus of claim 6 wherein the first lock is a clamp activated by manipulation of the first handle.

8. The apparatus of claim 5 wherein the first handle communicates with the cradle support to selectively rotate the cradle support about the second axis.

9. The apparatus of claim 1 wherein the base includes means for engaging a table of the medical imaging machine.

10. The apparatus of claim 1 further including a first scale indicating an amount of rotation of the head cradle with respect to the base about the rotation axis.

11. The apparatus of claim 1 wherein the cradle support having a second bearing allowing the head cradle to rotate about a second axis perpendicular to the rotation axis and further including a second scale indicating rotation about the second axis from a predetermined position.

12. The apparatus of claim 1 further including a fiducial marker mounted to the fixture detectable by the medical imaging machine.

13. The apparatus of claim 12 wherein the fiducial marker is mounted to the head cradle to indicate rotation of the head cradle.

14. The apparatus of claim 1 wherein the bearing surfaces follow at least a portion of a surface of a cylinder, the cylinder being coaxial about the rotation axis.

15. The apparatus of claim 1 further including a mat fitting against a patient table to support a torso of the patient and sized in height to straighten the patient's cervical spine when the patient's head is supported in the head cradle.

16. The apparatus of claim 15 wherein the mat is detachable from the base.

17. A fixture for adjusting a patient's head position in a medical imaging machine comprising:
   a base;
   a first support and a second support attached to the base and extending upwardly from the base;
   an outer ring having a first central axis and an inner surface sized to encompass a patient's head, wherein the outer ring is rotatably mounted between the first and the second supports to control angulation of the first central axis; and
   an inner ring including a support for rotating the patient's head, the inner ring having a second central axis and an outer surface sized to fit rotationally within the outer ring to rotate the patient's head with respect to the outer ring, wherein the first and second central axes are aligned;
   wherein the inner and outer ring are constructed of a material to allow imaging therethrough.

18. The fixture of claim 17 further including: a rollable bearing element; and at least a first race sized to engage the bearing formed in one of the inner surface of the outer ring and the outer surface of the inner ring, wherein the bearing is formed of a material to allow imaging therethrough.

19. The fixture of claim 18 wherein the rollable bearing element is at least one ball.

* * * * *